US 6,591,701 B2

(12) United States Patent
Suga (10) Patent No.: US 6,591,701 B2
(45) Date of Patent: Jul. 15, 2003

(54) WEATHERING TEST APPARATUS HAVING A LONG-ARC TYPE AIR-COOLED VERTICAL METAL HALIDE LAMP

(75) Inventor: Nagaichi Suga, Toyko (JP)

(73) Assignee: Suga Test Instruments Co., Ltd., Tokyo (JP)

(*) Notice: Subject to any disclaimer, the term of this patent is extended or adjusted under 35 U.S.C. 154(b) by 351 days.

(21) Appl. No.: 09/750,106

(22) Filed: Dec. 29, 2000

(65) Prior Publication Data

US 2002/0083782 A1 Jul. 4, 2002

(51) Int. Cl.$^7$ ............................................... G01N 25/00
(52) U.S. Cl. ...................................... 73/865.6
(58) Field of Search ........................ 73/865.6, 865.8, 73/159; 313/17, 22, 24, 35, 36

(56) References Cited

U.S. PATENT DOCUMENTS

| | | | |
|---|---|---|---|
| 3,983,742 A | * 10/1976 | Suga | .................. 73/865.6 |
| 4,817,447 A | * 4/1989 | Kashima et al. | |
| 4,823,050 A | 4/1989 | English et al. | |
| 4,859,899 A | 8/1989 | Keeffe et al. | |
| 4,864,180 A | 9/1989 | English et al. | |
| 4,931,655 A | * 6/1990 | Yoshida et al. | |
| 5,220,840 A | * 6/1993 | Neigoff et al. | |
| 5,503,032 A | * 4/1996 | Tikhtman et al. | .......... 73/865.6 |

FOREIGN PATENT DOCUMENTS

JP          0068082      * 5/1979    ................. 313/24

* cited by examiner

Primary Examiner—Robert Raevis
(74) Attorney, Agent, or Firm—Wenderoth, Lind & Ponack, L.L.P.

(57) ABSTRACT

A weathering test apparatus having a vertically disposed long-arc type air-cooled metal halide lamp, a lamp housing having a cooling device for cooling a lower seal portion of the lamp, and a vertical specimen rack which rotates about the lamp. The lamp, in which halide metals and mercury and a rare gas are infused, includes a supporting member having at least one hollow protrusion positioned at the upper ½ to ⅔ portion of the radiation length of a radiation tube wall, and the radiation length of the lamp is 5 cm to 15 cm. The lamp housing comprises an air supply device disposed outside of the test chamber for supplying cooling air, a cooling device located between an inner optical filter and the lower seal portion of the lamp, and an air volume adjustment device. In this way, the temperature difference between the upper seal portion of the lamp and the lower seal portion of the lamp may be decreased.

16 Claims, 12 Drawing Sheets

PRIOR

FIG.3
PRIOR

WEATHERING TEST APPARATUS HAVING A LONG-ARC TYPE AIR-COOLED VERTICAL METAL HALIDE LAMP

BACKGROUND OF THE INVENTION

1. Field of the Invention

The present invention relates to a weathering test apparatus for conducting weathering tests and light-fastness tests and, in particular, to an apparatus using an air-cooled metal halide lamp as a radiant energy source for the weathering tests.

2. Description of the Related Art

As to the kinds of radiant energy sources of a weathering test apparatus that tests the weatherability and the color fastness of materials, common ISO/JIS standards describe an enclosed carbon arc lamp, a sunshine carbon arc lamp, and a xenon arc lamp. In the weathering test and the light-fastness test, the correlation between the outdoor or indoor exposure test and the accelerated test with an apparatus is important to determine the life and durability of materials and products.

Thereupon, each radiant energy source spectrum simulates the sunlight spectrum by means of a combination of various kinds of glass filters. For example, the radiation at wavelengths less than 275 NM is cut off in the case of an exterior materials test, and the radiation at wavelengths less than 295 NM is cut off in the case of an interior materials test.

However, as the weatherability and the light-fastness of materials and products have been improved in recent years, a longer period of time is required to obtain a test result. And thus, it is necessary to provide a more accelerated weathering test apparatus.

Therefore, interest in a weathering test apparatus that a metal halide lamp as the radiant energy source is increasing. This is because the metal halide lamp produces radiation energy that is approximately 30 or more times stronger from 300 NM to 400 NM than that of the above described enclosed carbon arc lamp, sunshine carbon arc lamp, and xenon arc lamp.

The weathering test apparatus with the metal halide lamp is primarily used for a screening test. The metal halide lamp may include an air-cooled type and a water-cooled type. And the kind of lamp housing for the lamp can be an air-cooled type and a water-cooled type. Further, a metal halide lamp whose rating is 2 kW, 4 kW, 6 kW is generally used. The metal halide lamp is a long-arc straight-tube style air-cooled type, and the associated tube is small. The lamp is used in a horizontal position. Also, the lamp housing that cools the lamp with water has a double-tube structure and includes an inner optical filter and an outer optical filter, which arrange a spectral distribution of the radiant energy source. The above-mentioned general weathering test apparatus with the metal halide lamp is a combination of the air-cooled lamp and the water-cooled lamp housing.

Japanese Patent No. 2,942,444 describes two types of weathering test apparatuses using the above-mentioned long-arc type air-cooled metal halide lamp and the above-mentioned water-cooled lamp housing. The first type of weathering test apparatus, wherein the lamp is horizontally positioned in an upper portion of a test chamber and a specimen stage is horizontally fixed on a lower portion of the test chamber. The second type of weathering test apparatus, wherein the lamp is horizontally located in approximately the center of the test chamber and a horizontal specimen rack rotates about the lamp.

The prior art apparatus, however, does not include a weathering test apparatus that uses a vertically disposed long-arc type metal halide lamp. It is difficult to use the conventional long-arc type metal halide lamp in a vertical orientation, because halide metals in the lamp accumulate in a lower portion of the lamp, and thus the spatial distribution curve of luminous intensity becomes uneven.

Some short-arc and low wattage type metal halide lamps are used in a vertical orientation. The maximum radiation length of the short-arc type is 3 cm. However, the short-arc type is for illumination and point-source light. Therefore, the radiant energy of the visible radiation part is too strong for an effective weathering test. Also, it is necessary to put specimens on the small spherical spatial distribution curve of luminous intensity, but practically speaking, this is rather difficult. In particular, it is difficult to use the conventional short-arc type vertical metal halide lamp by extension of the radiation length for weathering tests, because the lamp cannot be properly cooled. A radiation tube of the lamp is disposed inside an outer tube of the lamp, and heating. Therefore, halide metals in the lamp tend to gather in a lower portion of the lamp and a spatial distribution curve of luminous intensity becomes uneven.

Also, in the case of weathering tests, the spectral energy distribution of the radiant energy source must simulate the spectral distribution of sunlight. And so, glass filters are always needed to arrange the spectral distribution. The lamp housing, which is not only a water-cooled type but also an air-cooled type, is necessarily a double-tube structure comprising the inner optical filter and the outer optical filter. In the case of the water-cooled type, the filters provide a flow of cooling water and a specified spectral energy distribution. In the case of the air-cooled type, the filters provide a flow of cooling air and a specified spectral energy distribution.

The above-mentioned water-cooled lamp housing is a more complex structure than the air-cooled type, but nevertheless has a high cooling efficiency.

However, when the long-arc type air-cooled vertical metal halide lamp whose rating 2 kW or 3 kW is lighted in the above double-tube structure type lamp housing, the life of the lamp is very short.

As a result, we analyzed the lamp having a short life, and found that the molybdenum thin film in a lower seal portion of the lamp, which acts as the electric conductor between the electrodes and a lead wire, is damaged or the lower electrode of the lamp changes to an abnormal color, i.e. the lower electrode becomes blackened, and some parts of tube are damaged. As mentioned above, the abnormally discolored portion was concentrated on the lower part of the lamp.

Applicant measured the temperature at three locations of the lamp housing, i.e. an air entrance, an upper seal portion of the lamp, and a lower seal portion of the lamp. And, as a result of several measurements, it was discovered that the temperature difference between the upper seal portion of the lamp and the lower seal portion of the lamp exceeded 100° C. The reason for the temperature difference is that the temperature of warmed air in the upper seal portion of the lamp increases due to the heat of a radiation part while warm air passes through the radiation part and reaches the lower seal portion of the lamp.

Then, Applicant tried to increase the cooling air volume from a blower. As a result, the temperature of the upper seal portion of the lamp and the temperature of the lower seal portion of the lamp were reduced. However, it is impossible to solve the problem of the temperature difference between the upper seal portion of the lamp and the lower seal portion of the lamp by increasing the cooling air volume. The temperature difference creates an abnormal convection in the tube. The abnormal convection causes an abnormal temperature distribution in the radiation part and an adhesion of the enclosed halide metals to the lower electrode. The abnormal temperature distribution in the radiation part causes an abnormal spatial distribution curve of luminous intensity, in other words, abnormal lighting. The abnormal lighting results in incorrect test results. Accordingly, the test accuracy of the device is reduced.

SUMMARY OF THE INVENTION

It is an object of the present invention to provide a weathering test apparatus which comprises a long-arc type air cooled vertical metal halide lamp and a lamp housing for the lamp and a vertical specimen rack which rotates about the lamp, which is centrally located in the housing.

To this end, Applicant has developed a new weathering test apparatus having a long-arc type air-cooled metal halide lamp in which halide metals and mercury and a rare gas are infused. The lamp comprises a supporting member having at least one hollow protrusion positioned at the upper half to upper two thirds of the radiation length of a radiation tube wall. The radiation length of the lamp is 5 cm to 15 cm. The lamp lights in a vertical orientation.

Also, an inner ring of a lower metal fitting is mounted to the lamp housing.

A cooling device is positioned in the inner ring of the lower metal fitting. The cooling device is capable of adjusting the volume of air from an air supply device, located outside of the test chamber, and cooling the lower seal portion of the lamp by blowing cooling air. The inner ring of the lower metal fitting is located between an inner optical filter and the lower seal portion of the lamp. The cooling device is positioned such that cooling air impinges on the center of the lower seal portion of the lamp. By the present invention, the cooling device decreases the temperature difference between the upper seal portion of the lamp and the lower seal portion of the lamp.

If the cooling device is positioned at an upper part of the lower seal portion of the lamp, it is possible to influence the temperature distribution in the radiation part of the lamp, and to cause an unstable radiation energy distribution. Also, in the case where the cooling device is positioned at the lower part of the lower seal portion of the lamp, the cooling device is only able to cool the bottom of the lower metal fitting. However, when the cooling device is positioned at the lower part of the lower seal portion of the lamp, the cooling device is not able to decrease the temperature difference between the lower seal portion of the lamp and the upper seal portion of the lamp.

The air volume of the blower can be selectively adjusted in order to send cooling air into the space between the lamp and the inner optical filter. Also, the air volume of the air supply device mounted outside the test chamber can be selectively adjusted to send cooling air to the cooling device.

In the case of the air-cooled type lamp housing, the lamp is cooled by open-air, the changing of the open-air temperature, and the air volume to influence the cooling capability. Therefore, an air volume adjustment device is added to selectively adjust the air volume in order to maintain the proper temperature of the upper seal portion of the lamp and the proper temperature of the lower seal portion of the lamp. Further, in the case of the air-cooled type lamp housing, dust that is suspended in air will be inhaled by the cooling device, and thus, the dust soils the lamp and the filters. Therefore, it is necessary to attach an air filter on the blower and the air supply device.

BRIEF DESCRIPTION OF THE DRAWINGS

Other objects and advantages of the invention will become apparent upon reading the attached detailed description and upon reference to the drawings in which.

DETAILED DESCRIPTION OF THE INVENTION

Figure 1:
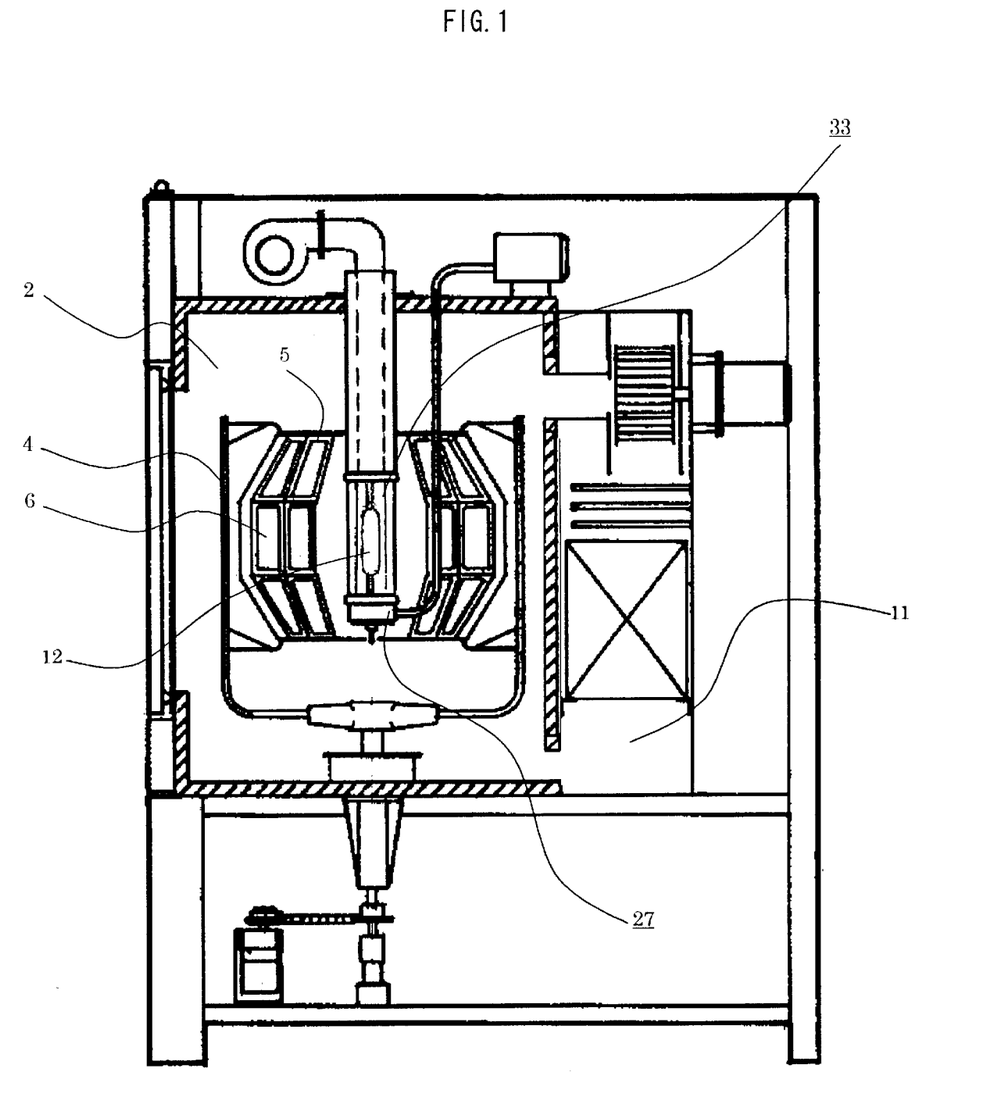
FIG. 1 is a schematic cross-sectional view of a first embodiment of a weathering test apparatus according to the present invention.

FIG. 1 shows the basic construction of a weathering test apparatus of the present invention. The weathering test apparatus shown in FIG. 1 includes a long-arc type air-cooled vertical metal halide lamp 12, as a radiant energy source. The weathering test apparatus of the present invention includes a lamp housing 33, a test chamber 2, and a vertical specimen rack 4. The lamp 12 is located along the central vertical axis of the test chamber 2. The lamp 12 is positioned in the lamp housing 33, and the vertical specimen rack 4 surrounds the lamp housing. The vertical specimen rack 4 is rotatable about the lamp 12. A specimen holder 5 for holding specimens 6 is attached to the vertical specimen rack 4. The lamp 12 is positioned at the central axis of the vertical specimen rack 4 in order to provide a specified spectral energy distribution. Also, an air conditioning chamber 11, which circulates conditioned air and controls temperature and humidity, is in communication with the test chamber 2. The weathering test apparatus of the present invention comprises a cooling device 27.

Figure 2:
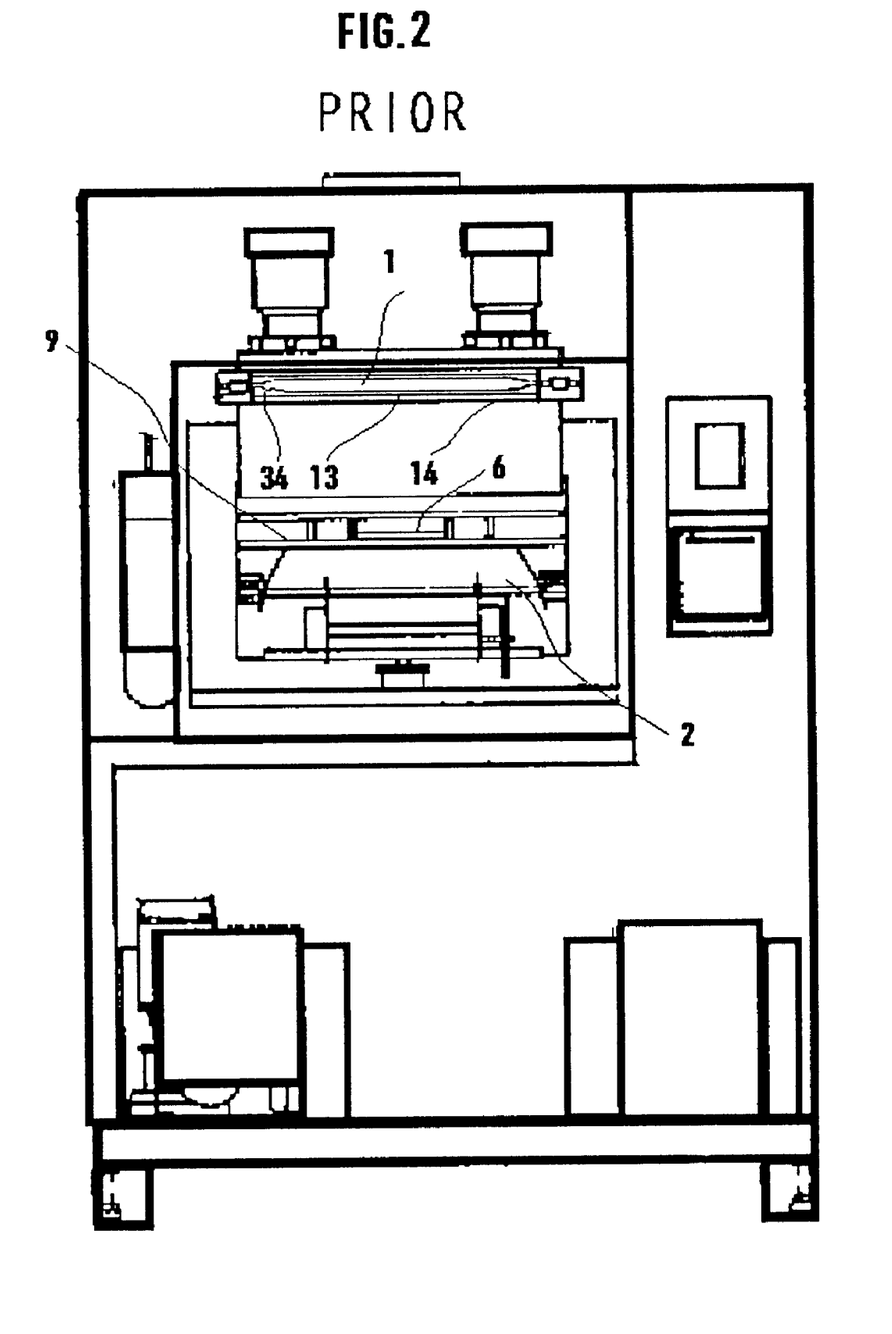
FIG. 2 is a schematic cross-sectional view of a conventional weathering test apparatus having a stationary specimen stage and a long-arc type air-cooled horizontal metal halide lamp and a water-cooled lamp housing.

For comparison with the present invention, FIG. 2 shows a conventional weathering test apparatus having a stationary specimen stage 9 and a long-arc type water-cooled horizontal metal halide lamp 1 disposed in a water-cooled lamp housing 34. The long-arc type water-cooled horizontal metal halide lamp 1 serves as the radiant energy source and is horizontally positioned on an upper portion of the test chamber 2. The stationary specimen stage 9 is positioned horizontally below the lamp 1. Specimens 6 are mounted on the stationary specimen stage 9, and the surfaces of the specimens are directed upwards. The water-cooled lamp housing 34, which is a water-cooled type, has a double-tube structure formed of an inner optical filter 13 and an outer optical filter 14, which are mounted on the water-cooled lamp housing 34. Excess heat is removed from the lamp 1 by recirculating distilled or deionized water between the inner optical filter 13 and the outer optical filter 14 in conjunction with an air flow provided along the lamp 1.

The exposure area of the conventional weathering test apparatus shown in FIG. 2 is 790 $cm^2$. The exposure area of the present invention, as shown in FIG. 1 is 5670 $cm^2$. Thus, the exposure area provided by the present invention is 7.16 times that of the conventional exposure area.

Figure 3:
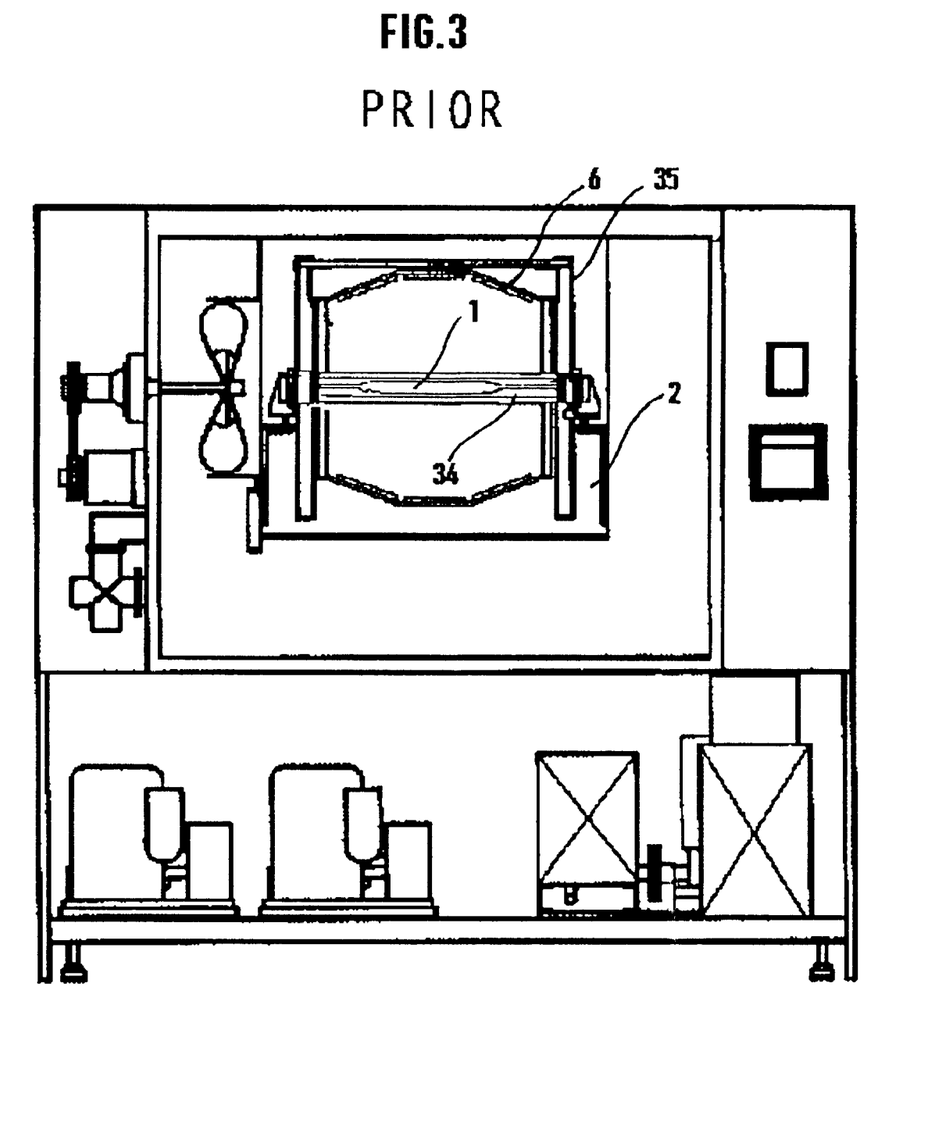
FIG. 3 is a schematic cross-sectional view of another conventional weathering test apparatus having a horizontal specimen rack and a long-arc type air-cooled horizontal metal halide lamp and a water-cooled lamp housing.

FIG. 3 shows another conventional weathering testing apparatus having a horizontal specimen rack 35 and a long-arc type air-cooled horizontal metal halide lamp 1 disposed in a water-cooled lamp housing 34 for comparison with the present invention. The long-arc type air-cooled horizontal metal halide lamp 1 serves as the radiant energy source and is horizontally located in approximately the center of the test chamber 2. The conventional weathering test apparatus includes the specimens 6, and the horizontal specimen rack 35, which rotates about the centrally located lamp 1. The lamp 1 is positioned along the central axis of the horizontal specimen rack 35. Also, the lamp 1 has a rated power of 2 kW, or 4 kW, or 6 kW. The radiation part of the lamp is a long-arc type. The lamp 1 is an air-cooled straight-tube type whose tube aperture is small. The water-cooled lamp housing 34, which is a water-cooled type, has a double-tube structure.

Figure 4:
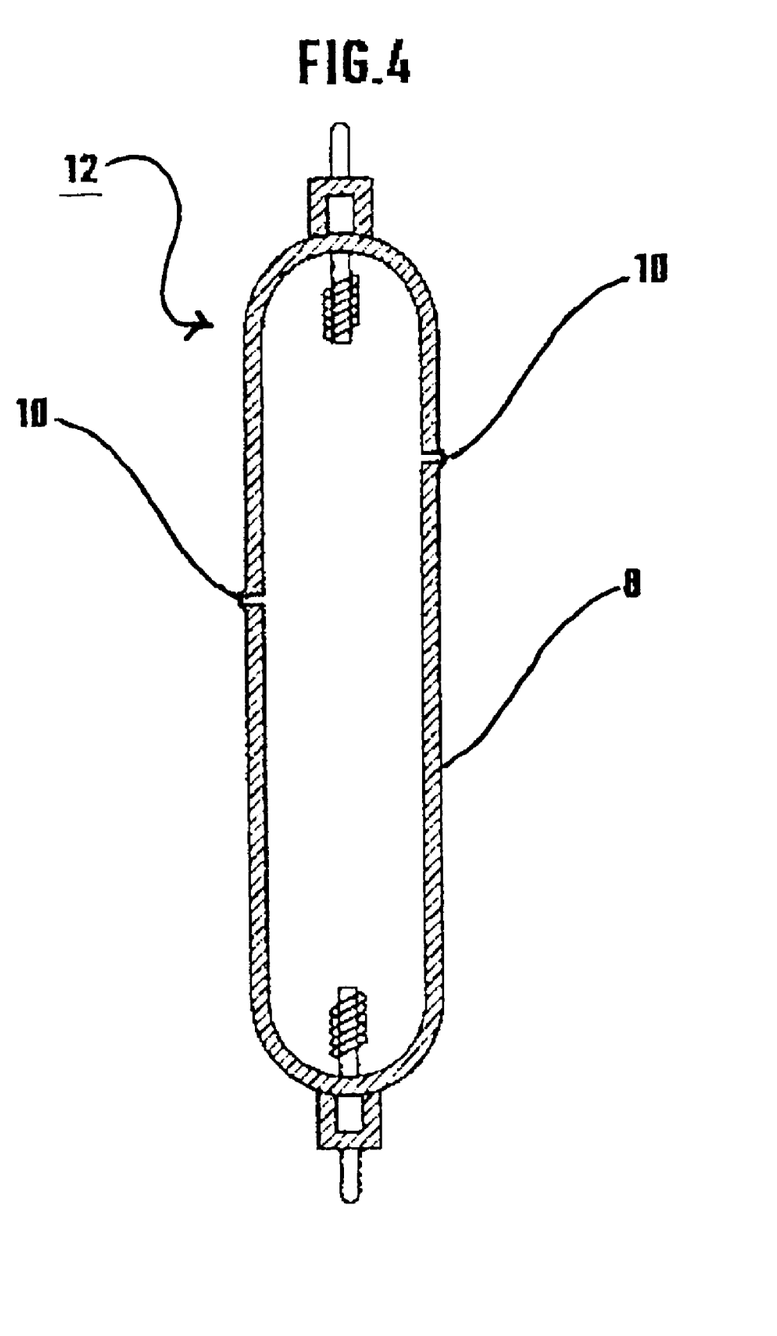
FIG. 4 is a schematic cross-sectional view of a vertical metal halide lamp of the first embodiment according to the present invention shown in FIG. 1.

FIG. 4 shows the vertical metal halide lamp of the first embodiment according to the present invention as shown in FIG. 1.

As discussed above, the lamp of the first embodiment according to the present invention is a long-arc type air-cooled vertical metal halide lamp 12 into which halide metals and mercury and a rare gas are infused. The lamp 12 has a radiation tube wall 8, and a supporting member having at least one hollow protrusion 10 positioned at the upper half to two thirds of the radiation length of the radiation tube wall 8. Also, the radiation length of the lamp is 5 cm to 15 cm, and the lamp 12 lights in a vertical orientation.

Figure 5:
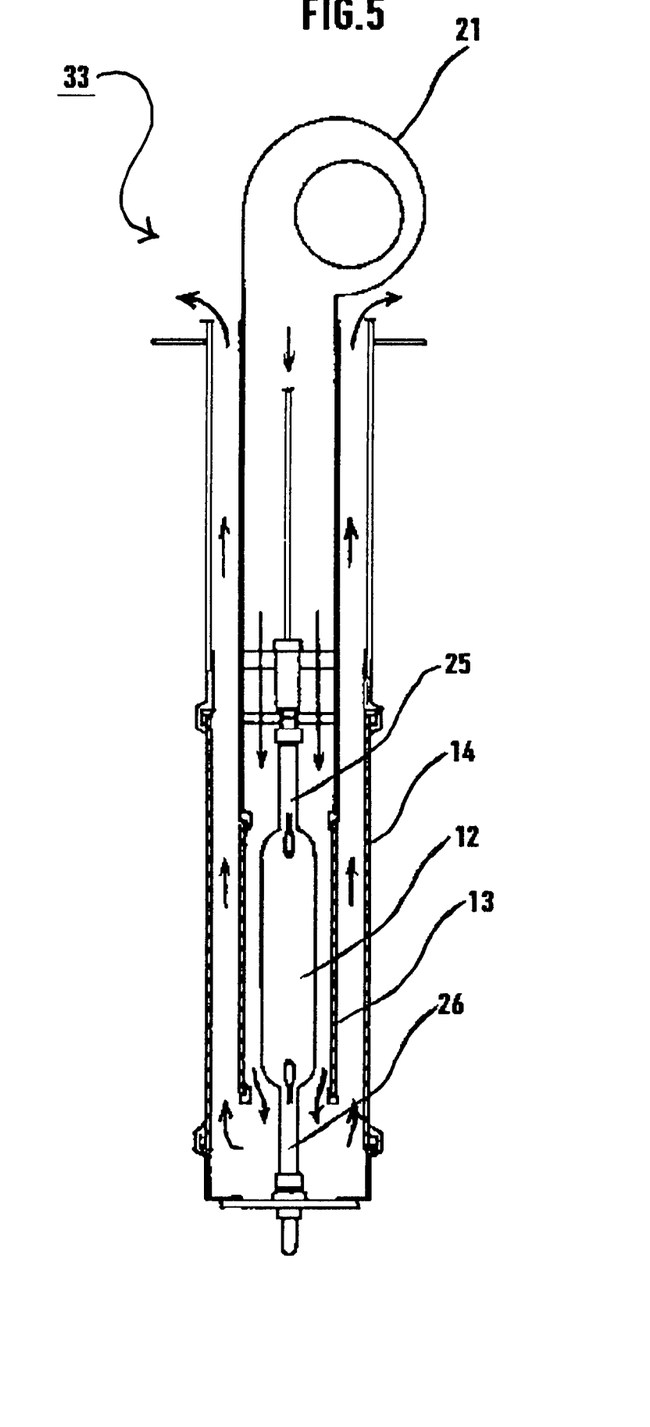
FIG. 5 is a schematic cross-sectional view indicating the vertical metal halide lamp shown in FIG. 4 with the conventional lamp housing having a structure as shown in FIG. 3.

FIG. 5 shows the long-arc type air-cooled vertical metal halide lamp 12, as shown in FIG. 4, with the conventional lamp housing having a structure as shown in FIG. 3. The lamp housing 33 is a double-tube structure, and is air-cooled. Note, the arrows in FIG. 5 show the flow of air through the housing. The lamp housing 33 includes the inner optical filter 13 and the outer optical filter 14. The structure of the lamp housing 33 is similar to the structure of the water-cooled lamp housing 34 shown in FIG. 2. The inner optical filter 13 and the outer optical filter 14 are cylindrical and provide cooling-air flow paths and a specified energy distribution. Also, a first blower 21 and the long-arc type air-cooled vertical metal halide lamp 12 are attached to the housing 33. The lamp housing 33 has an upper seal portion and a lower seal portion 26 for the lamp 12.

When Applicants tested the life of the lamp using the lamp housing 33 and the lamp 12, it was not sufficiently long.

Figure 6:
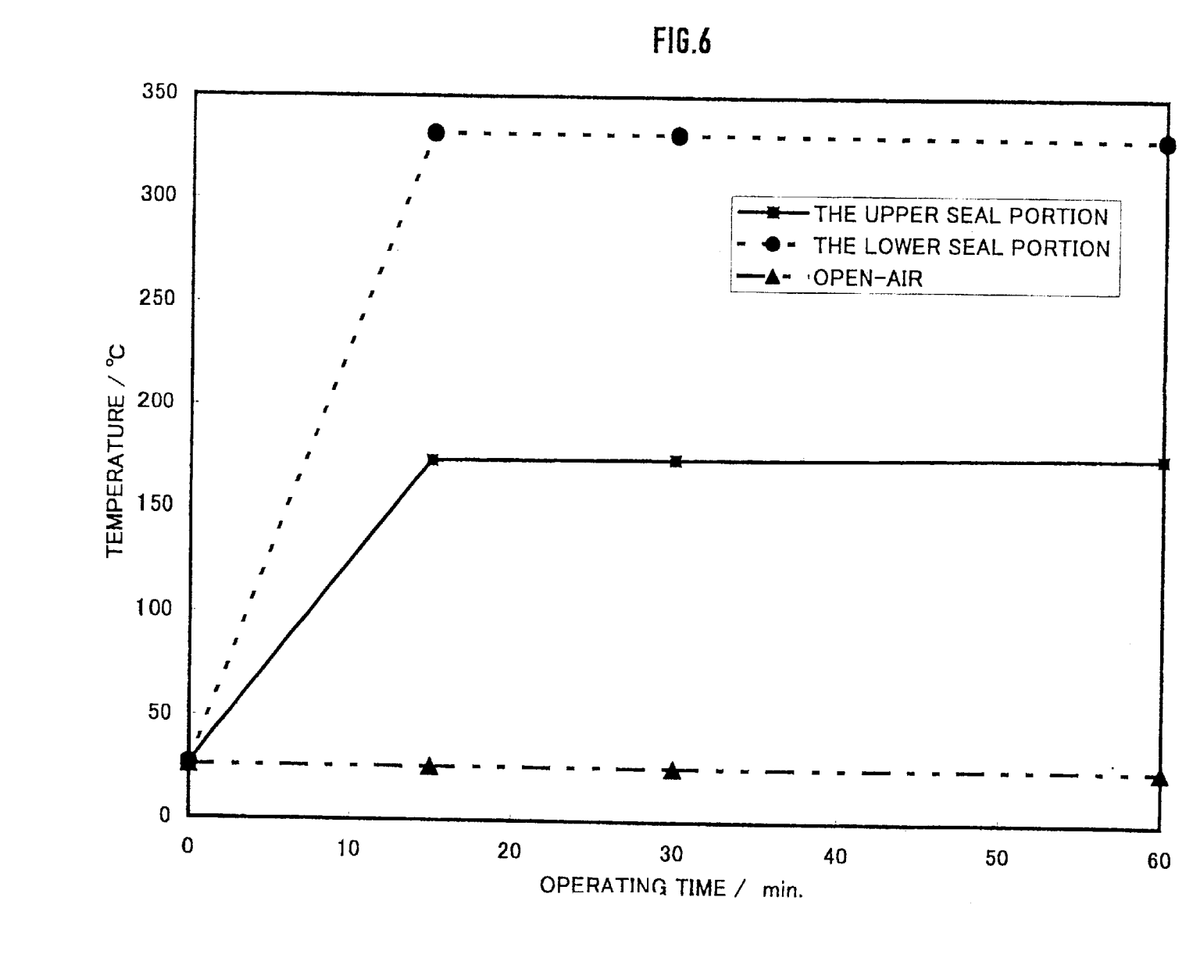
FIG. 6 is a X-Y graph of the time-temperature relation of two parts, which are an upper seal portion of the lamp and a lower seal portion of the lamp, of the conventional lamp housing with the vertical metal halide lamp shown in FIG. 5.

FIG. 6 shows an X-Y graph of the time-temperature relation of two parts, which are the upper seal portion of the lamp and the lower seal portion of the lamp, of the conventional lamp housing, which has the long-arc type air-cooled vertical metal halide lamp 12 shown in FIG. 5. FIG. 6 shows that the temperature of the lower seal portion of the lamp exceeded 330° C. A molybdenum thin film is sealed with glass at the lower seal portion of the lamp. The molybdenum thin film acts as the electric conductor between a lead wire connected to an igniter outside of the test chamber and an electrode in the radiation tube. The heatproof temperature of the molybdenum thin film is designed to be 350° C. The life of the lamp and the temperatures of the electrode and the area around the lead wire are related to each other. The life of the lamp becomes extremely short when the temperature of the electrode and the temperature around the lead wire are high. The temperature of the lower seal portion of the lamp should be maintained below 250° C.

In FIG. 6, the temperature of the lower seal portion of the lamp is almost at the heatproof limit temperature of the molybdenum thin film, and Applicant has concluded that it causes the life of the lamp to be extremely short.

FIG. 7(a) shows the lamp housing of the first embodiment according to the present invention as shown in FIG. 1. The arrows in FIG. 7(a) show the flow of air through the housing.

The lamp housing 33 is for the long-arc type air-cooled vertical metal halide lamp 12 which serves as the radiant energy source. The diameter of the inner optical filter 13 is 60 mm so that it encloses the lamp 12 and is spaced from the outer diameter of the radiation part of the lamp. A first air channel 28 is formed between the lamp 12 and the inner optical filter 13, which are concentrically disposed. And the outer optical filter 14, whose diameter is 100 mm, is outside of the inner optical filter 13. The diameter of the outer optical filter 14 is larger than the diameter of the inner optical filter 13 such that a second air channel 29 is formed between the inner optical filter 13 and the outer optical filter 14.

The lamp housing 33 comprises an upper metal fitting 15, a lower metal fitting 16, an upper metal fitting band 17 and a lower metal fitting band 18. The lamp 12, the inner optical filter 13 and the outer optical filter 14 are sandwiched between the upper metal fitting 15 and the lower metal fitting 16, and are fixed in place with the upper fitting metal band 17 and the lower metal fitting band 18. The lower end parts of a first cylinder 19 and a second cylinder 20 are jointed or connected with the upper metal fitting 15. The first cylinder 19 has the same diameter as the inner optical filter 13, and extends vertically upward through the center of the test chamber ceiling, and is open at its upper end. The first cylinder 19 is made of metal.

The second cylinder 20 has the same diameter as the outer optical filter 14, and extends vertically upward through the center of the test chamber ceiling, and is open at its upper end. The second cylinder 20 is also made of metal.

The first blower 21 is mounted on the open upper end of the first cylinder 19. The first blower 21 sucks in open-air, and the air, which is sucked in by the first blower 21 and adjusted to an optional air volume, enters the first cylinder 19 and passes through the first air channel 28. After the air reaches the lower metal fitting 16, the air flows upward through the second air channel 29, between the first cylinder 19 and the second cylinder 20 and is exhausted outside of the test chamber.

As shown in FIG. 7(b), a cooling device 27 is connected to and extends through the lower metal fitting 16. The cooling device 27 comprises an air nozzle 30, an air volume adjustment device 24, a heat-resistant polytetrafluoroethylene tube, and the air pump 23. The lower metal fitting 16 comprises a first inner ring 31 of the lower metal fitting 16. The first inner ring 31 fixes the inner optical filter 13. The upper seal portion of the lamp 25 and the lower seal portion of the lamp 26 are attached to the lamp housing. The cooling device 27 is mounted interiorly of the inner fitting ring 31, namely, between the lower seal portion 26 of the lamp 12 and the inner optical filter 13.

As shown in FIGS. 7(a)–(b), an air pump 23 is mounted outside of the test chamber for the purpose of supplying air through the heat-resistant polytetrafluoroethylene tube. The lower seal portion 26 of the lamp 12 is cooled by the cooling device blowing cooling air, the volume of which is adjusted by the air supply device. The air volume adjustment device 24 is for adjusting the volume of the air supplied by air pump 23. The air volume adjustment device is added to maintain the proper temperature of the upper seal portion 25 and the proper temperature of the lower seal portion 26.

Also in the case of the air-cooled type of lamp, dust in air may be sucked in by the cooling device and then soil the lamp 12 and the filters 13, 14 and may influence the results of a test. Therefore, a clean air filter (not shown) should be attached on each of the first blower 21 and the air pump 23.

As shown in FIG. 7(b), the heat-resistant polytetrafluoroethylene tube penetrates the side wall of the lower metal fitting 16, and the air nozzle 30 is positioned in the lamp housing so as to surround the lower seal portion 26 of the lamp 12. Further, the air nozzle 30, which is made of metal, extends vertically upward to a position that is not in contact with the lower seal portion 26 of the lamp 12. In particular, the air nozzle 30 has a horizontal ring-form portion that is coaxially positioned about the center of the lower seal portion 26 of the lamp 12. In the present invention, stainless steel is preferably used for the air nozzle 30. The ring form part of the air nozzle 30 surrounds the lower seal portion 26 of the lamp 12. The air nozzle 30 is connected to the heat-resistant polytetrafluoroethylene tube. The heat-resistant polytetrafluoroethylene tube is connected to the air pump 23 and the air volume adjustment device 24, which are mounted outside of the test chamber. The air is discharged from the air nozzle 30, and the air volume adjustment device 24, which is downstream from the air pump 23, is operable to adjust the volume of air supplied to the air nozzle 30.

Note that the lamp housing 33 can be assembled by the following steps. Step 1: inserting the lamp 12 into a center hole of the lower metal fitting 16; positioning the inner filter 13 in the first inner ring 31 of the lower metal fitting 16; positioning the outer filter 14 on the lower metal fitting 16; and fixing the outer filter 14 and the lower metal fitting with the lower fitting metal band 18. Step 2: positioning the inner filter 13 on the inner ring of the upper metal fitting 15, and the outer filter 14 on the upper metal fitting 15; and fixing the outer filter 14 and the upper metal fitting 15 with the upper metal fitting band 17. Step 3: inserting the first cylinder 19 in the upper metal fitting 15; and fixing the first and second cylinders to the upper metal fitting 15.

Figure 8:
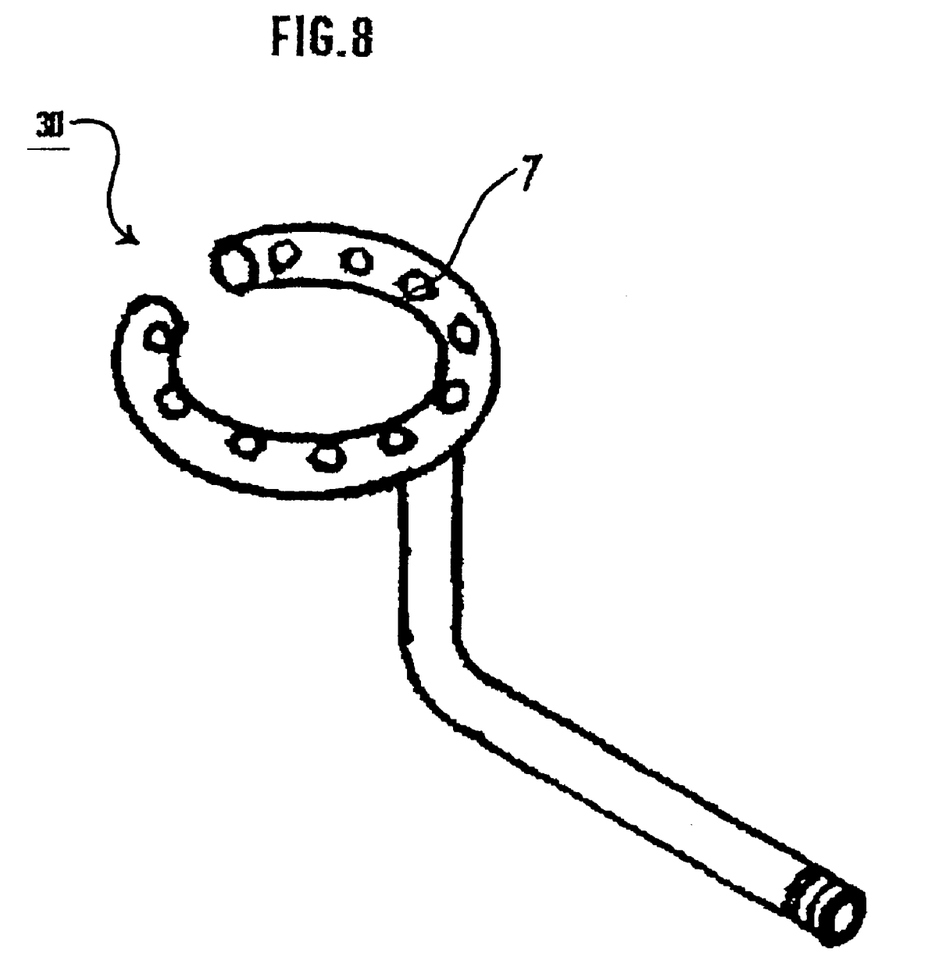
FIG. 8 is a schematic perspective view of an air nozzle of the first embodiment according to the present invention shown in FIG. 1.

FIG. 8 shows the air nozzle 30 of the first embodiment according to the present invention shown in FIG. 1. The air nozzle 30 has several apertures 7 formed on the inside of a ring, which forms part of the air nozzle 30.

Figure 7:
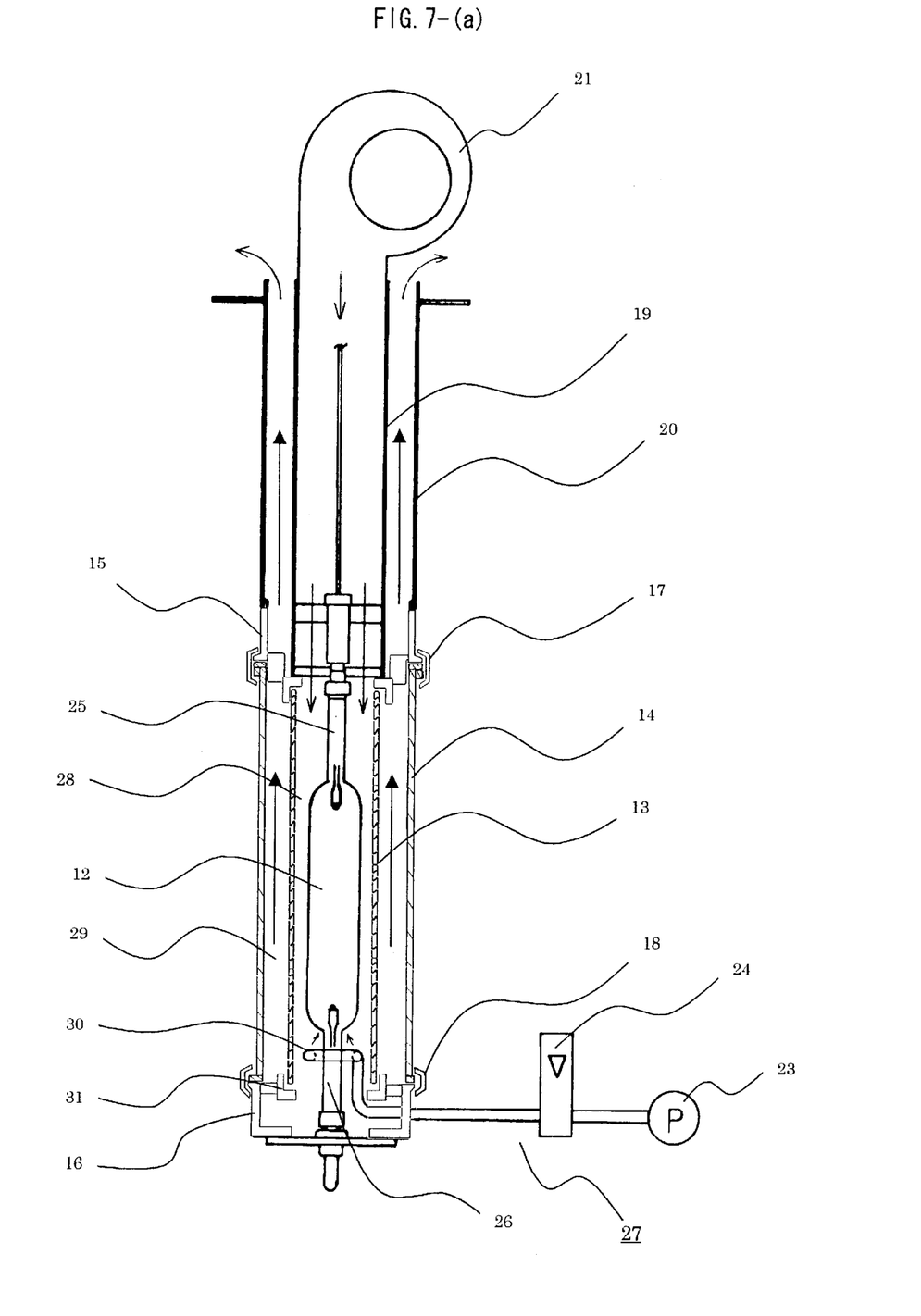
FIG. 7(a) is a schematic cross-sectional view of a lamp housing, constructed in accordance with the first embodiment of the present invention as shown in FIG. 1, and a cooling device.
FIG. 7(b) is a schematic illustration of the cooling device of the first embodiment of the present invention.
Figure 9:
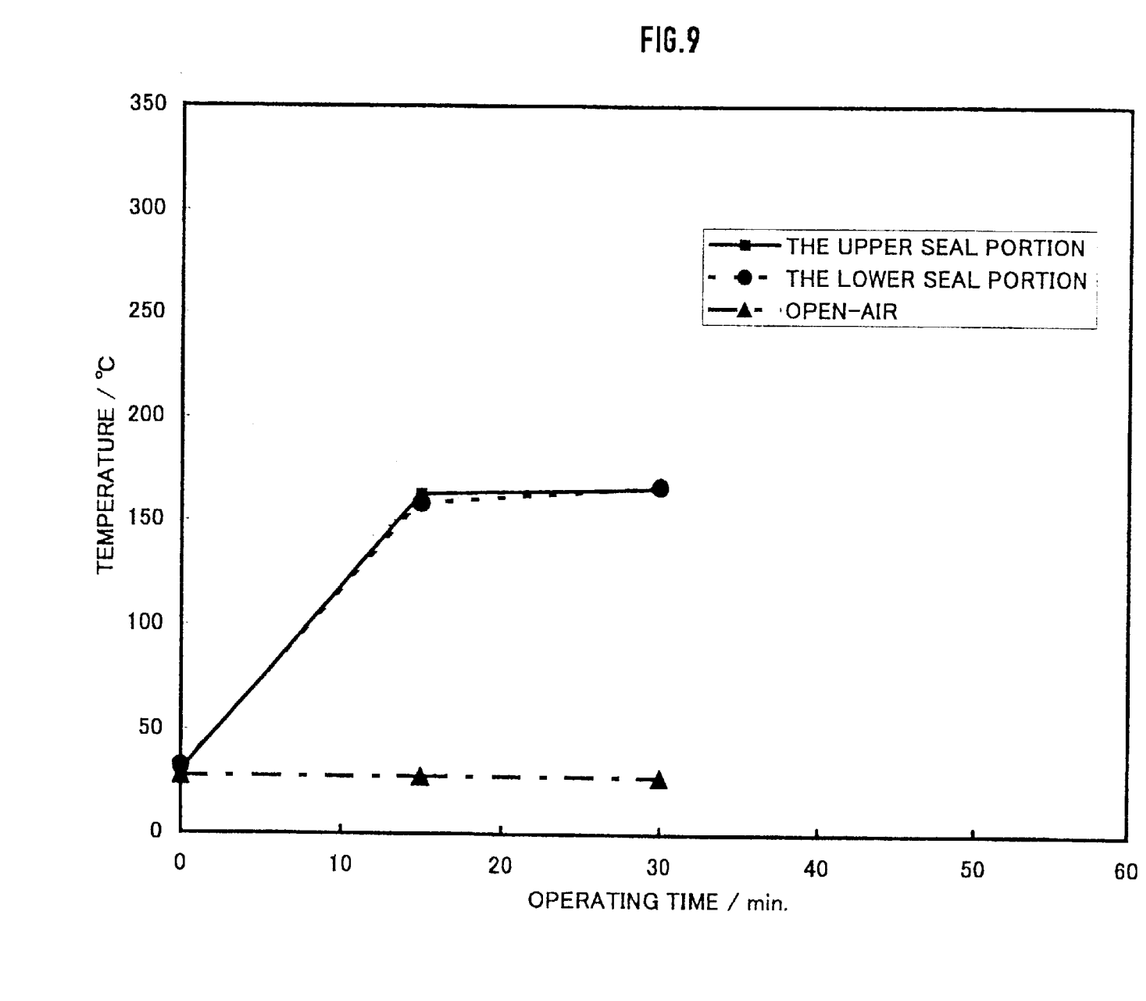
FIG. 9 is a X-Y graph of the time-temperature relation of two parts, which are the upper seal portion of the lamp and the lower seal portion of the lamp, of the present invention having the lamp housing with the vertical metal halide lamp shown in FIG. 7(a)

FIG. 9 is an X-Y graph of the time-temperature relationship of two parts, i.e. the upper seal portion of the lamp and the lower seal portion of the lamp, of the present invention having the lamp housing with the lamp 12 as shown in FIG. 7. FIG. 9 shows the measurement results of the temperature of the upper seal portion of the lamp and the lower seal portion of the lamp. The measurements were taken under the conditions that the air volume rate of the first blower is adjusted to 2100 l/min and the air volume rate of the air nozzle is adjusted to 50 l/min. FIG. 9 indicates that the temperature difference between the upper seal portion of the lamp and the lower seal portion of the lamp is decreased by the present invention.

Figure 10:
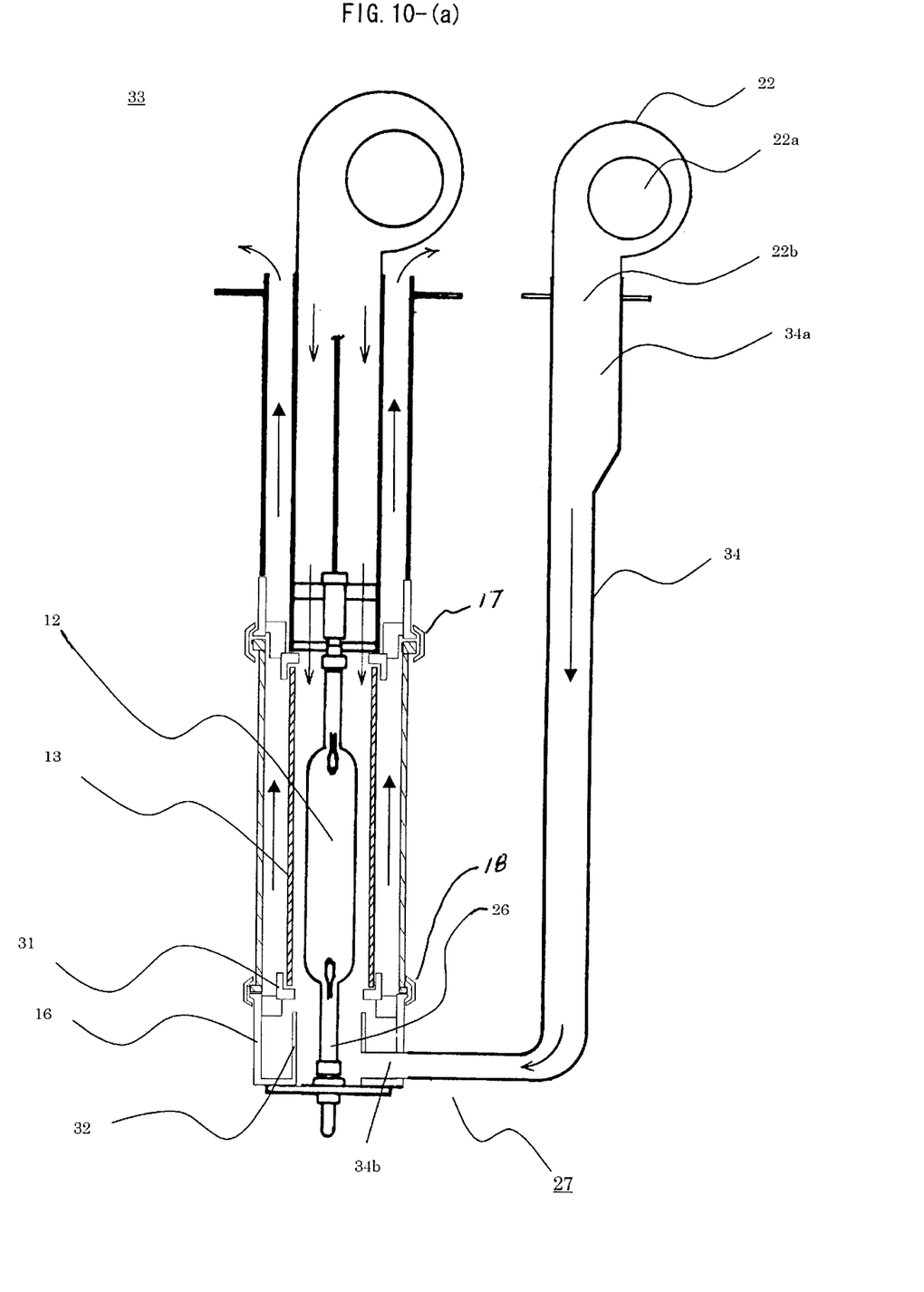
FIG. 10(a) is a schematic cross-sectional view of a lamp housing, constructed in accordance with a second embodiment of the present invention, and a cooling device.
FIG. 10(b) is a schematic illustration of the cooling device of the second embodiment of the present invention.

FIG. 10(a) shows a lamp housing constructed in accordance with a second embodiment of the present invention. The arrows in FIG. 10 show the flow of air through the housing. As shown in FIG. 10(b), another type of cooling device is attached to the lamp housing 33. Each element shown in FIGS. 10(a)–(b) is the same as the elements of the first embodiment shown in FIG. 1, with the exception of the cooling device. The cooling device of the second embodiment is a ventilation duct system, which is composed of a second blower 22 as the air supply device, and a duct 34. The second blower 22 is mounted outside of the test chamber. The cooling device of the ventilation duct system is different from the cooling device of the air nozzle system shown in FIG. 7(a). The cooling device of the ventilation duct system is positioned interiorly of the circumference of a first inner ring 31 of the lower metal fitting 16, i.e. between the lower seal portion 26 of the lamp 12 and the inner optical filter 13. The cooling device is capable of blowing cooling air, whose volume is adjusted by the second blower 22, to cool the lower seal portion 26 of the lamp 12.

The second blower 22 comprises air inlet 22a and air outlet 22b. The duct 34 comprises air inlet 34a and air outlet 34b. The second blower 22 is mounted outside of the test chamber, and the air outlet 22b is connected to the air inlet 34a of the duct 34. The flow passage defined by the duct becomes narrower in a direction toward the lamp housing. The air outlet 34b of the duct is inserted into an opening formed through the sidewall of the lower metal fitting 16 and is connected to a wall of a second inner ring 32 of the lower metal fitting 16. The air is supplied from the second blower 22, and the supplied air, whose volume is adjustable, passes through the duct 34, reaches the interior of second inner ring 32, and cools the lower seal portion 26 of the lamp 12.

The weathering testing apparatus of the present invention comprises the vertically-mounted metal halide lamp as the radiant energy source and the vertical specimen rack that rotates about the centrally disposed lamp. The weathering test apparatus of the present invention further comprises the cooling device for cooling the lower seal portion of the lamp. The cooling device comprises the air supply device, which may take the form of an air nozzle style or a ventilation duct style. Therefore, as shown in FIG. 9, the temperature difference of the upper seal portion of the lamp and the lower seal portion of the lamp may be decreased from over 100° C. to 5° C.

Also, the temperature of the molybdenum thin film can be maintained below 250° C. which is a proper temperature.

Accordingly, a temperature condition which can cause the destruction of the molybdenum thin film, i.e. a disconnection, can be avoided so as to result in longer life of the lamp.

The temperature distribution in a radiation part of the lamp becomes even, causing the temperature difference of the upper seal portion of the lamp and the lower seal portion of the lamp to be decreased.

The even temperature distribution in the radiation part of the lamp increases the even distribution of halide metals in the radiation part, and leads to an even spatial distribution curve of luminous intensity. The even spatial distribution curve of luminous intensity is able to achieve a good test result.

While the invention has been described in connection with certain preferred embodiments, it will be understood that there is no intention to limit the invention to the embodiments shown, but it is intended, on the contrary to cover the various alternative and equivalent constructions included within the spirit and scope of the appended claims.

I claim:

1. A weathering test apparatus comprising:
   a test chamber;
   a lamp housing disposed in said test chamber;
   a long-arc type air-cooled metal halide lamp vertically disposed in said lamp housing; and
   a rotatable specimen rack surrounding said lamp housing, said rotatable specimen rack being capable of rotating about a central axis of said lamp,
   wherein said lamp housing is an air-cooled lamp housing which comprises:
      an inner optical filter surrounding said lamp such that the diameter of the radiation part of said lamp is spaced from an inner peripheral surface of said inner optical filter;
      a first air channel defined between said lamp and said inner optical filter;
      an outer optical filter surrounding and spaced from said inner optical filter;
      a second air channel defined between said inner optical filter and said outer optical filter;
      upper and lower metal fittings sandwiching said lamp, said inner optical filter and said outer optical filter;
      an upper fixing ring fixing in position said outer optical filter, said inner optical filter and said lamp, said upper fixing ring being positioned at a top of said outer optical filter, said inner optical filter, and said lamp; and
      a lower fixing ring fixing in position said outer optical filter, said inner optical filter, and said lamp, said lower fixing ring being positioned at a bottom of said outer optical filter, said inner optical filter, and said lamp.

2. A weathering test apparatus as claimed in claim 1, wherein said long-arc type air-cooled metal halide lamp comprises:
   a radiation tube having a tube wall;
   an infusion of halide metals and mercury and a rare gas; and
   at least one hollow protrusion formed in an upper half to two thirds of a radiation length of said tube wall, said radiation length being 5 cm to 15 cm.

3. A weathering test apparatus as claimed in claim 1, wherein said air-cooled lamp housing further comprises:
   a first metal cylinder having an open upper end and extending vertically upward from said inner optical filter through a center of a ceiling of said test chamber, wherein said first metal cylinder and said inner optical filter have equal diameters; and
   a second metal cylinder having an open upper end and extending vertically upward from said outer optical filter through the center of said test chamber ceiling, wherein said second cylinder and said outer optical filter have equal diameters.

4. A weathering test apparatus as claimed in claim 3, further comprising:
   a first blower mounted on the open upper end of said first metal cylinder; and
   a cooling air supply device, mounted outside of said test chamber, for supplying an adjustable volume of cooling air in the vicinity of a lower seal portion of said lamp.

5. A weathering test apparatus as claimed in claim 4, wherein said cooling air supply device comprises:
   a cooling air delivery device, attached to said lower metal fitting, for delivering the cooling air; and
   an air volume adjustment device, connected to said cooling air delivery device, for permitting adjustment of the volume of air supplied from said cooling air supply device.

6. A weathering test apparatus as claimed in claim 5, wherein air from said first blower flows downward through said first metal cylinder and said first air channel, and can be adjusted to an optimal air volume that advances upward through said second air channel after reaching said lower metal fitting, and is then exhausted outside of said test chamber.

7. A weathering test apparatus as claimed in claim 5, wherein said cooling air supply device further comprises an air pump, and said air delivery device comprises an air nozzle formed of metal.

8. A weathering test apparatus as claimed in claim 7, further comprising a flow meter disposed downstream from said air pump, wherein the flow of air from said air pump is adjusted by said flow meter.

9. A weathering test apparatus as claimed in claim 5, wherein said air delivery device penetrates a side wall of said lower metal fitting and extends upward vertically toward said lower seal portion of said lamp.

10. A weathering test apparatus as claimed in claim 9, wherein said air delivery device terminates in a ring-shaped air discharge portion that substantially surrounds but does not contact said lower seal portion of said lamp.

11. A weathering test apparatus as claimed in claim 10, wherein said ring-shaped air discharge portion lies in a horizontal plane.

12. A weathering test apparatus as claimed in claim 10, wherein said ring-shaped air discharge portion includes a plurality of apertures located at an inner side of said ring-shaped air discharge portion.

13. A weathering test apparatus as claimed in claim 4, wherein lower metal fitting includes a first inner ring supporting a lower end of said inner optical filter.

14. A weathering test apparatus as claimed in claim 4, wherein lower metal fitting includes a first inner ring and a second inner ring, said first inner ring supporting a lower end of said inner optical filter.

15. A weathering test apparatus as claimed in claim 14, wherein said air supply device comprises a second blower and a duct connected to an air outlet of said second blower, wherein said duct defines a flow passage that becomes narrower in a cooling air discharge direction, said duct having an air outlet portion extending through a hole formed in a side wall of said lower metal fitting, and said air outlet is connected to a wall of said second inner ring of said lower metal fitting.

16. A weathering test apparatus as claimed in claim 14, wherein said side wall of said lower metal fitting surrounds and is concentric with said second inner ring of said lower metal fitting.

\* \* \* \* \*